(12) United States Patent
Iki et al.

(10) Patent No.: US 7,063,720 B2
(45) Date of Patent: Jun. 20, 2006

(54) COVERED STENT WITH CONTROLLED THERAPEUTIC AGENT DIFFUSION

(75) Inventors: Kobi Iki, San Carlos, CA (US); Marshall Tsuruda, San Jose, CA (US)

(73) Assignee: The Wallace Enterprises, Inc., Nashville, TN (US)

( * ) Notice: Subject to any disclaimer, the term of this patent is extended or adjusted under 35 U.S.C. 154(b) by 101 days.

(21) Appl. No.: 10/941,064

(22) Filed: Sep. 14, 2004

(65) Prior Publication Data
US 2006/0058870 A1 Mar. 16, 2006

(51) Int. Cl.
A61F 2/06 (2006.01)
(52) U.S. Cl. ..................................... 623/1.46
(58) Field of Classification Search ........ 623/1.1–1.15, 623/1.42–1.46; 424/422–426, 457–468; 427/2.24–2.28
See application file for complete search history.

(56) References Cited

U.S. PATENT DOCUMENTS

| | | | |
|---|---|---|---|
| 4,300,244 A | 11/1981 | Bokros | |
| 4,553,545 A | 11/1985 | Maass et al. | |
| 5,282,823 A | 2/1994 | Schwartz et al. | |
| 5,286,254 A | 2/1994 | Shapland et al. | |
| 5,399,352 A | 3/1995 | Hanson | |
| 5,419,760 A | 5/1995 | Narciso, Jr. | |
| 5,433,909 A | 7/1995 | Martakos et al. | |
| 5,605,696 A | 2/1997 | Eury et al. | |
| 5,609,629 A | 3/1997 | Fearnot et al. | |
| 5,676,685 A | 10/1997 | Razavi | |
| 5,824,053 A | 10/1998 | Khosravi et al. | |
| 5,873,904 A | 2/1999 | Ragheb et al. | |
| 5,984,963 A | 11/1999 | Ryan et al. | |
| 5,993,489 A | 11/1999 | Lewis et al. | |
| 6,010,529 A | 1/2000 | Herwck et al. | |
| 6,027,516 A | 2/2000 | Kolobow et al. | |
| 6,149,681 A | 11/2000 | Houser et al. | |
| 6,165,212 A | 12/2000 | Dereume et al. | |
| 6,270,523 B1 | 8/2001 | Herweck et al. | |

(Continued)

FOREIGN PATENT DOCUMENTS

WO    WO 97/40755    11/1997

(Continued)

OTHER PUBLICATIONS

Wolgemuth, Lenny, "A Look at Parylene Coatings in Drug-Eluting Technologies", Medical Device and Diagnostic Industry, 2005, 6 pp, http://www.devicelink.com/mddi/archive/05/08/004.html.

*Primary Examiner*—Vy Bui
(74) *Attorney, Agent, or Firm*—James F. Hann; Haynes Beffel & Wolfeld LLP

(57) ABSTRACT

A covered stent includes a generally tubular stent body having inner and outer stent body surfaces. A sleeve of porous material encloses the stent body and has inner and outer portions opposed to the inner and outer stent body surfaces. A therapeutic agent is located along the stent body, the agent being diffusible through the material. A diffusion barrier is located between the inner material portion and the agent along the stent. The diffusion barrier prevents passage of at least a significant amount the agent through the inner portion of the sleeve of porous material. A diffusion restrictor is located between the outer portion of the sleeve of porous material and the agent along the stent. The diffusion restrictor permits passage of the agent through the inner material portion at a therapeutic level.

20 Claims, 3 Drawing Sheets

U.S. PATENT DOCUMENTS

| | | |
|---|---|---|
| 6,273,913 B1 | 8/2001 | Wright et al. |
| 6,299,604 B1 | 10/2001 | Ragheb et al. |
| 6,358,276 B1 | 3/2002 | Edwin |
| 6,663,662 B1 * | 12/2003 | Pacetti et al. ............... 623/1.13 |
| 6,712,845 B1 * | 3/2004 | Hossainy ................... 623/1.42 |
| 2003/0109917 A1 | 6/2003 | Rudin et al. |
| 2003/0185964 A1 | 10/2003 | Weber et al. |
| 2004/0024416 A1 | 2/2004 | Yodfat et al. |

FOREIGN PATENT DOCUMENTS

| | | |
|---|---|---|
| WO | WO 98/08482 | 3/1998 |
| WO | WO 03/007840 A2 | 1/2003 |

* cited by examiner

COVERED STENT WITH CONTROLLED THERAPEUTIC AGENT DIFFUSION

CROSS-REFERENCE TO OTHER APPLICATIONS

This is related to the following: U.S. patent application Ser. No. 09/740,597 filed Dec. 19, 2000; U.S. patent application Ser. No. 09/910,703 filed Jul. 20, 2001; U.S. Pat. No. 6,248,122 B1 issued Jun. 19, 2001; U.S. Pat. No. 6,238,430 issued May 29, 2001; U.S. Pat. No. 6,645,237 issued Nov. 11, 2003; and U.S. Pat. No. 6,572,648 issued Jun. 3, 2003.

FEDERALLY SPONSORED RESEARCH OR DEVELOPMENT

None.

BACKGROUND OF THE INVENTION

The present invention provides for the delivery of a therapeutic agent by a covered stent to a target site within a hollow body structure of the patient, particularly within the vascular system for the treatment of cardiovascular and peripheral vascular disease, such as vascular stenoses and restenoses, dissections and other tissue separation conditions, aneurysms, and the like.

Research has been done to determine the causes and possible treatments of coronary restenosis following balloon angioplasty. Restenosis following balloon angioplasty is believed to result from several causes, including elastic recoil of the vessel, thrombus formation and cell wall growth. The article, Chan, A W, Chew, D P, and Lincoff, A M, Update on Pharmacology for Restenosis, *Current Interventional Cardiology Reports* 2001, 3:149–155, concludes that restenosis remains a major problem for percutaneous coronary intervention and that while drug-eluting stents may be found to be effective, larger clinical trials are needed.

The apparatus of the present invention, however, are also useful for placement in other hollow body structures, such as the ureter, urethra, bronchus, biliary tract, gastrointestinal tract and the like, for the treatment of other conditions which may benefit from the introduction of a therapeutic agent along with a reinforcing or protective structure within the body lumen. The prostheses will typically be placed endoluminally. As used herein, "endoluminally" will mean placement by percutaneous or cutdown procedures, wherein the prosthesis is transluminally advanced through the body lumen from a remote location to a target site in the lumen. In vascular procedures, the prostheses will typically be introduced "endovascularly" using a catheter over a guidewire under fluoroscopic, or other imaging system, guidance. The catheters and guidewires may be introduced through conventional access sites to the vascular system, such as through the femoral artery, or brachial and subclavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures may be provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces of a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art.

The dimensions of a typical endoluminal prosthesis will depend on its intended use. Typically, the prosthesis will have a length in the range from 0.5 cm to 15 cm, usually being from about 0.8 cm to 10 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 50 mm, preferably being in the range from about 3 mm to 15 mm for vascular applications and from about 25 mm to 45 mm for aortic applications.

One type of endoluminal prosthesis includes both a stent component and a covering component. These endoluminal prostheses are often called stent grafts or covered stents. A covered stent is typically introduced using a catheter with both the stent and covering in contracted, reduced-diameter states. Once at the target site, the stent and covering are expanded. After expansion, the catheter is withdrawn from the vessel leaving the covered stent at the target site. Coverings may be made of, for example, PTFE, ePTFE or Dacron® polyester.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small and large diameter vessels, porous fluoropolymers, such as ePTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated and removed. One balloon expandable stent is the Palmaz-Schatz stent available from the Cordis Division of Johnson & Johnson. Stents are also available from Medtronic AVE of Santa Rosa, Calif. and Guidant Corporation of Indianapolis, Ind.

BRIEF SUMMARY OF THE INVENTION

The present invention is directed to a covered stent including a generally tubular stent body having inner and outer stent body surfaces. A sleeve of porous material encloses the stent body. The sleeve of material has inner and outer portions opposed to the inner and outer stent body surfaces. A therapeutic agent is located along the stent body, the agent being diffusible through the material. A diffusion barrier is located between the inner material portion and the agent along the stent. The diffusion barrier prevents passage of at least a significant amount the agent through the inner portion of the sleeve of porous material. A diffusion restrictor is located between the outer portion of the sleeve of porous material and the agent along the stent. The diffusion restrictor permits passage of the agent through the outer material portion at a therapeutic level.

The therapeutic agent may be part of a therapeutic agent/silicone carrier matrix secured to, that is adhered to or otherwise in intimate contact with, the stent body. The therapeutic agent may comprise a hydrophilic anti-restenosis drug, preferably at least one of Sodium Nitroprusside, L-Arginine or Poly L-Arginine. Thus, the invention provides for the controlled, stent-based release of a hydrophilic compound using a covered stent in a vascular/aqueous environment. The diffusion restrictor and the diffuser barrier may both comprise Par ylene. The diffusion barrier may be a substantially non-porous vapor-deposited layer of Parylene and the diffusion restrictor may be a micro-porous vapor-deposited layer of Parylene.

Various features and advantages of the invention will appear from the following description in which the preferred embodiments have been set forth in detail in conjunction with the accompanying drawings.

DETAILED DESCRIPTION OF THE INVENTION

Figure 1:
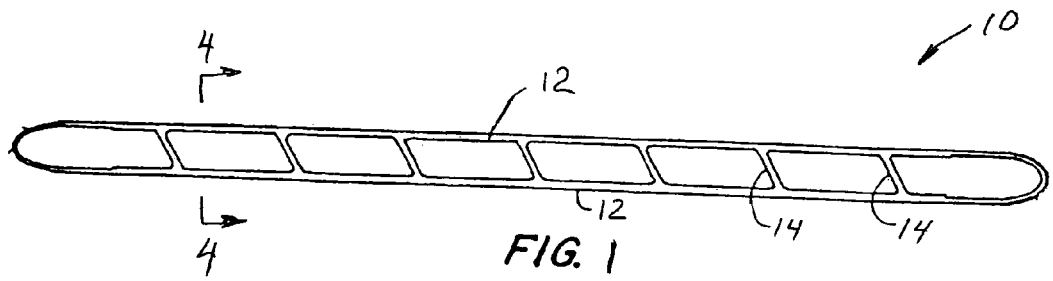
FIG. 1 illustrates a conventional ladder type stent blank.
Figure 2:
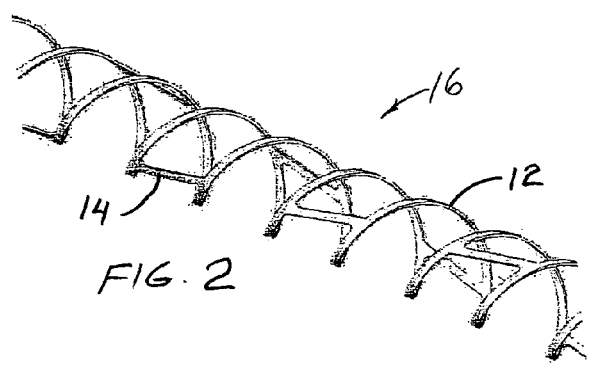
FIG. 2 illustrates the stent blank of FIG. 1 formed into a generally helical coil.
Figure 3:
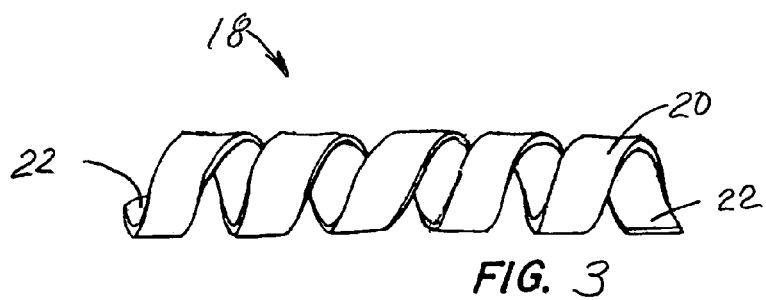
FIG. 3 shows a covered stent including a coiled stent as in FIG. 2 covered by a sleeve of material.

FIG. 1 illustrates a ladder type stent blank 10 having side edges or rails 12 connected by connectors or rungs 14. Stent blank 10 is shown to include two side rails 12; three or more side rail elements may also be used. Stent blank 10 is typically formed into an open spiral as shown in FIG. 2 to create a generally tubular ladder stent 16. Stent blank 10 may also be formed into a tighter wrapped generally tubular spiral so that side rails 12 lie generally adjacent to one another. To create the covered stent 18 of FIG. 3, a sleeve of porous graft-type material 20, such as made of ePTFE, is typically slid over stent blank 10 prior to forming stent blank 10 into the spiral shape of FIG. 2. The ends 22 of material 20 are typically sealed in an appropriate manner, such as by the use of an appropriate adhesive or by using other bonding techniques.

Figure 4:
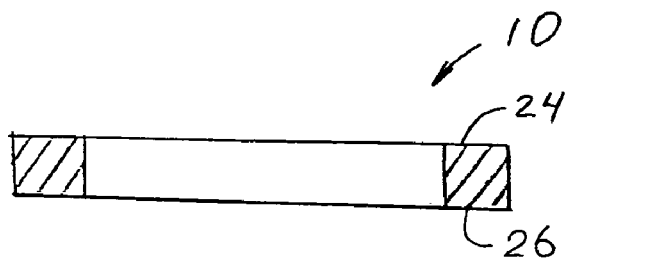
FIG. 4 is a cross sectional view of a stent blank taken along line 4—4 of FIG. 1.
Figure 5:
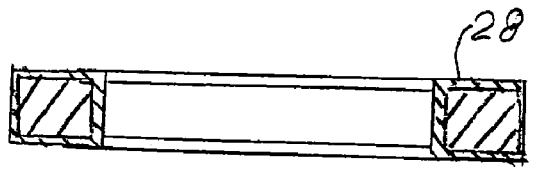
FIG. 5 shows the stent of FIG. 4 after a silicone/therapeutic matrix material has been applied thereto.
Figure 6:
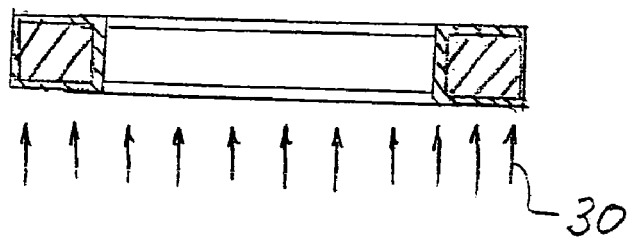
FIG. 6 illustrates the application of a diffusion barrier material to an inner stent body surface of the structure of FIG. 5.

The above-described structure is generally conventional. With the present invention stent blank 10 is treated as discussed with reference to FIGS. 4–7, typically prior to being enclosed within material 20. FIG. 4 is an enlarged cross sectional view of stent blank 10 having an outer stent body surface 24 and an inner stent body surface 26. A therapeutic agent, such as one or more of Sodium Nitroprusside, L-Arginine and Poly L-Arginine, is applied to stent blank 10. This is typically accomplished using a matrix of silicone or other matrix and the therapeutic agent applied as a liquid or semi-solid composition to stent blank 10. The composition is then stabilized, typically cured or polymerized, resulting in stent blank 10 being general uniformly covered with a silicone/therapeutic agent matrix 28. Stent blank 10 need not be uniformly covered but could have the therapeutic agent applied only to outer stent body surface 24. Also, multiple layers of the same, or different, therapeutic agent may be used with stent blank 10. This would provide flexibility in the delivery of one or more therapeutic agents. For example, the agent could be delivered in a multi-modal release with, for example, an initial bolus type delivery followed by at least one extended release phase.

After the application of matrix 28, a diffusion barrier material 30 is applied to at least inner stent body surface 26, and may be applied to all surfaces of stent blank 10 except for outer stent body surface 24. Diffusion barrier material 30 is provided to prevent passage of at least a significant amount of the therapeutic agent within matrix 28 from being diffused therethrough. A preferred diffusion barrier material is Parylene applied as a vapor. The thickness of diffusion barrier material 30 using Parylene is preferably greater than about 3.5 micrometers thick and is typically about 3–5 micrometers thick. At these thicknesses, the Parylene is an effectively uninterrupted later of Parylene and therefore sufficiently nonporous to act as an effective barrier to the passage of the therapeutic agent.

Figure 7:
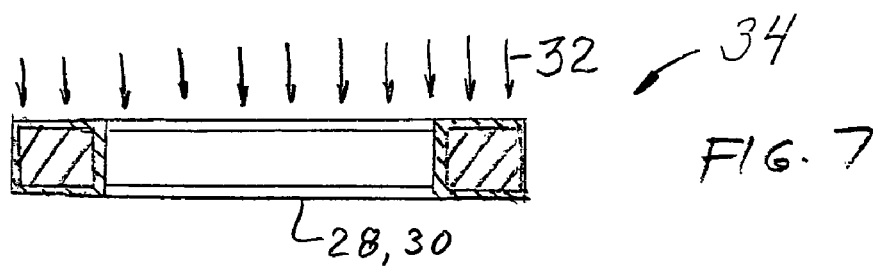
FIG. 7 illustrates the application of a diffusion restrictor material to an outer stent body surface of the stent of FIG. 6 to create a stent structure.

FIG. 7 illustrates application of a diffusion restrictor material 32 to outer stent body surface 24. Material 32 is used to restrict or otherwise control the passage of the therapeutic agent from matrix 28 at surface 24. A preferred diffusion restrictor material is also Parylene applied as a vapor. The thickness of diffusion restrictor material 32 comprising Parylene is preferably less than about 2.5 micrometers thick and is typically about 1–3 micrometers thick. At these thicknesses, material 32 is not an interrupted layer but has pinhole-like openings to create an effectively porous diffusion restrictor. The resulting stent structure 34 comprises stent blank 10 covered by matrix 28 over which diffusion barrier material 30 and diffusion restrictor material 32 have been applied. Thereafter, stent structure 34 is enclosed within material 20, see FIG. 8, and then coiled to create covered stent 18.

Diffusion barrier material 30 and diffusion restrictor material 32 may be made so that barrier material 30 prevents any measurable diffusion of the applicable agent through it while restricting material 32 permits diffusion of the agent at a first, therapeutic rate for the intended therapy. However, barrier material 30 typically allows the diffusion of some of the agent through it, but at a second rate, the second rate being less than the first, therapeutic rate. In one embodiment the second rate is at least 50% less than the first rate. The acceptable percentage will depend on various factors including the therapeutic agent used, the patient's condition, state of the disease, vascular flow, target site, the particular prior therapy, and so forth.

Figure 8:
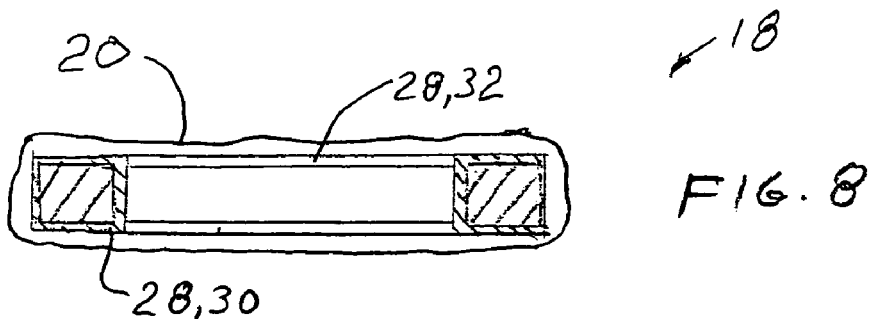
FIG. 8 shows the stent structure of FIG. 7 after being covered with a sleeve of porous material.
Figure 9:
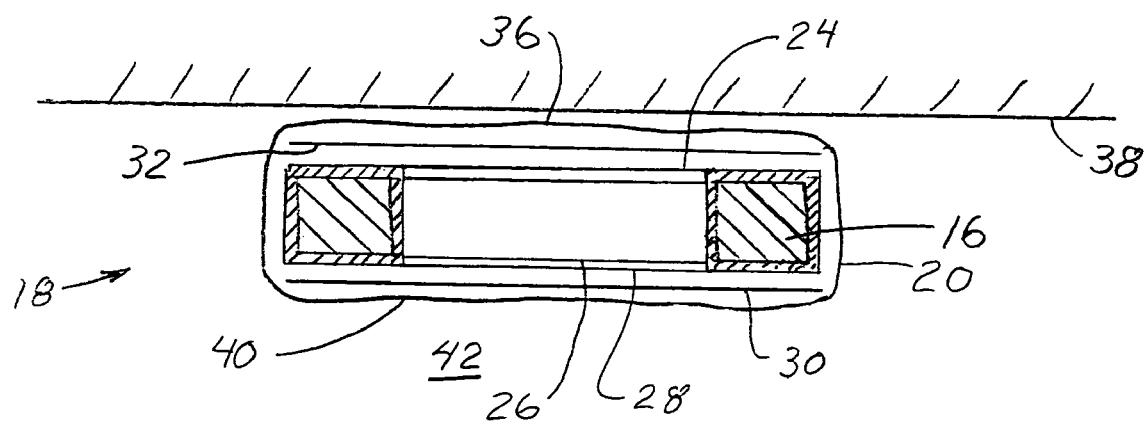
FIG. 9 is a simplified cross sectional view of a covered stent, similar to that of FIG. 8 with the various layers separated for purposes of illustration, positioned within a vessel and against the vessel wall.

FIG. 9 is a simplified cross sectional view of covered stent 18 similar to that of FIG. 8 with the various layers separated for purposes of illustration. Covered stent 18 is located within a vessel, such as a blood vessel, and with an outer material portion 36 of material 20 being positioned against the vessel wall 38 so that an inner material portion 40 of material 20 faces the open interior 42 of the vessel. Once in place against vessel wall 38, the therapeutic agent within matrix 28 may slowly diffuse through diffusion restrictor material 32 and outer material portion 36 and pass into a vessel wall 38. However, due to the use of diffusion barrier 30, diffusion of the therapeutic agent into interior 42 of the vessel is at least substantially reduced. This helps prevent wasting of the therapeutic agent as well as reducing or eliminating any negative consequences from the introduction of the therapeutic agent into vessel interior 42 and the systemic circulation.

Diffusion barrier material 30 and diffusion restrictor material 32 may be applied elsewhere, for example to the inner surface of inner material portion 40 or the inner surface of outer material portion 36, or both, instead of or in addition to application onto matrix-covered stent blank 10. In such case the therapeutic agent may be relatively loosely contained between diffusion barrier material 30 and stent blank 10 and between diffusion restrictor material 32 and stent blank 10.

Figure 11:
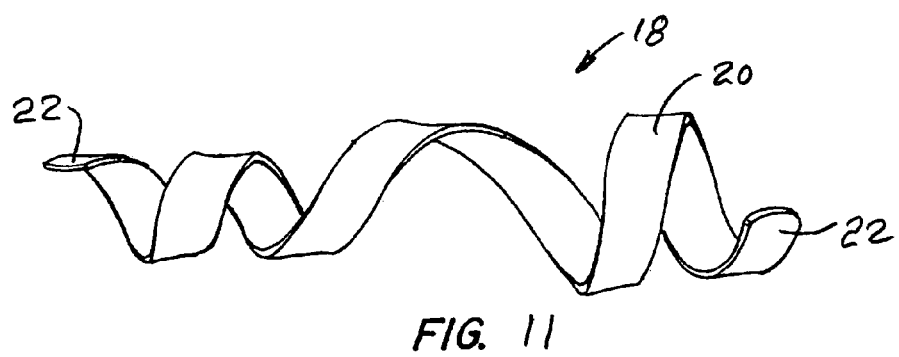
FIG. 11 shows an alternative to the covered ladder stent of FIG. 3.
Figure 10:
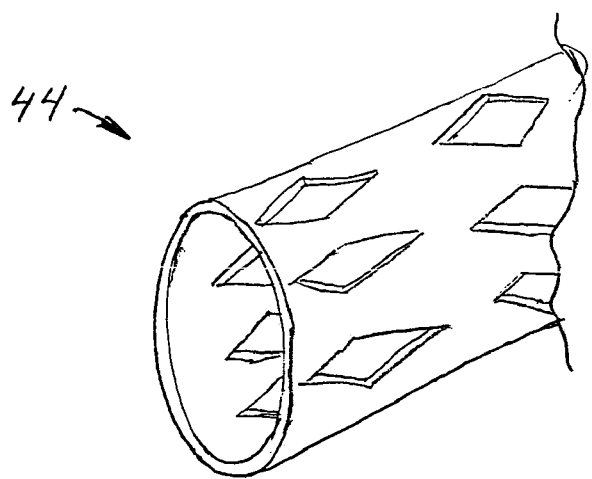
FIG. 10 is an overall view of an alternative stent body made of expanded metal.

The invention has been discussed with reference to a ladder-type stent 16. The invention may also be used with other types of stents, such as a cylindrical, expanded metal stent 44, shown in FIG. 10, having an appropriate sleeve of porous material covering both the inner and outer surfaces (not shown). FIG. 11 illustrates an alternative embodiment of the covered stent 18 of FIG. 3 having a variable pitch, that is different spacing between the turns, and a variable diameter.

Other modification and variation can be made to the disclosed embodiments without departing from the subject of the invention as defined in following claims.

Any and all patents, patent applications and printed publications referred to above are incorporated by reference.

What is claimed is:

1. A covered stent comprising:
    a generally tubular stent body having inner and outer stent body surfaces;
    a sleeve of porous material enclosing the stent body, the sleeve of material having inner and outer material portions opposed to the inner and outer stent body surfaces;
    a therapeutic agent along the stent body, the agent being diffusible through the sleeve of porous material;
    a diffusion restrictor between the outer material portion and the agent along the stent, said diffusion restrictor permitting passage of the agent through the inner material portion at a first, therapeutic rate; and
    a diffusion barrier between the inner material portion and the agent along the stent, said diffusion barrier preventing passage of the agent through the inner material portion at at most a second rate, the second rate being less than the first rate.

2. The covered stent according to claim 1 wherein the second rate is at least 50% less than the first rate.

3. The covered stent according to claim 1 wherein the stent body extends along a generally helical path.

4. The covered stent according to claim 3 wherein the sleeve of porous material extends along said generally helical path to define a covered stent structure having a length, the covered stent structure having turns, the covered stent structure defining a generally helical gap between the turns along at least substantially the entire length of the covered stent structure.

5. The covered stent according to claim 1 further comprising a silicone carrier carrying the agent.

6. The covered stent according to claim 1 wherein the agent comprises a hydrophilic agent.

7. The covered stent according to claim 1 wherein the agent comprises a hydrophilic anti-restenotic agent.

8. The covered stent according to claim 7 wherein the agent comprises at least one of Sodium Nitroprusside, L-Arginine and Poly L-Arginine.

9. The covered stent according to claim 1 wherein the agent adheres to the stent body.

10. The covered stent according to claim 9 wherein the diffusion barrier is applied onto the agent adhering to the stent body.

11. The covered stent according to claim 9 wherein the diffusion restrictor is applied onto the agent adhering to the stent body.

12. The covered stent according to claim 9 wherein the diffusion restrictor and the diffusion barrier are made of the same diffusion material.

13. The covered stent according to claim 12 wherein the diffusion material comprises Parylene.

14. The covered stent according to claim 13 wherein the diffusion barrier is greater than about 3.5 micrometers thick and the diffusion restrictor is less than about 2.5 micrometers thick.

15. The covered stent according to claim 13 wherein the diffusion barrier and the diffusion restrictor have different thicknesses with the diffusion barrier being about 3–5 micrometers thick and the diffusion restrictor being about 1–3 micrometers thick.

16. The covered stent according to claim 13 wherein the diffusion barrier comprises a substantially non-porous vapor-deposited layer of Parylene and the diffusion restrictor comprises a micro-porous vapor-deposited layer of Parylene.

17. A covered stent comprising:
    a generally tubular stent body having an inner and outer stent body surfaces;
    a sleeve of porous material enclosing the stent body, the sleeve of material having inner and outer material portions opposed to the inner and outer stent body surfaces;
    a hydrophilic anti-restenotic therapeutic agent/silicone carrier matrix adhering to the stent body, the agent being diffusible through the sleeve of porous material;

a diffusion restrictor applied onto the therapeutic agent/silicone carrier matrix along the stent, said diffusion restrictor permitting passage of the agent through the inner material portion at a first, therapeutic rate;

a diffusion barrier applied onto the therapeutic agent/silicone carrier matrix along the stent, said diffusion barrier preventing passage of the agent through the inner material portion at at most a second rate, the second rate being less than the first rate; and the diffusion restrictor and the diffuser barrier comprising Parylene.

18. The covered stent according to claim 17 wherein:

the diffusion barrier is greater than about 3.5 micrometers thick;

the diffusion restrictor is less than about 2.5 micrometers thick;

the stent body extends along a generally helical path;

the sleeve of the porous material extends along said generally helical path to define a covered stent structure having a length, the covered stent structure having turns, the covered stent structure defining a generally helical gap between the turns along at least substantially the entire length of the covered stent structure; and the agent comprises at least one of Sodium Nitroprusside, L-Arginine or Poly L-Arginine.

19. The covered stent according to claim 17 wherein the diffusion barrier comprises a substantially non-porous vapor-deposited layer of Parylene and the diffusion restrictor comprises a micro-porous vapor-deposited layer of Parylene.

20. The covered stent according to claim 17 wherein the second rate is at least 50% less than the first rate.

* * * * *